United States Patent [19]

Willhite, Jr. et al.

[11] Patent Number: 4,823,783

[45] Date of Patent: Apr. 25, 1989

[54] ADHESIVE-FREE BONDING OF CONTINUOUSLY MOVING WEBS TO FORM LAMINATE WEB AND PRODUCTS CUT THEREFROM

[75] Inventors: William Willhite, Jr., Cincinnati; Gerald M. Weber, Loveland; Godfrey Retier, Cincinnati, all of Ohio

[73] Assignee: The Procter & Gamble Company, Cincinnati, Ohio

[21] Appl. No.: 156,394

[22] Filed: Feb. 16, 1988

Related U.S. Application Data

[62] Division of Ser. No. 835,068, Feb. 28, 1986, abandoned.

[51] Int. Cl.$^4$ .............................................. A61L 15/00
[52] U.S. Cl. ..................................... 128/156; 428/40; 428/137; 428/192; 428/198; 428/280; 428/282; 428/284; 428/296; 428/299; 428/343; 428/354; 428/913; 604/372
[58] Field of Search ............... 428/137, 138, 280, 282, 428/284, 913, 343, 352, 354, 40, 192, 198, 296, 299; 128/156; 604/372

[56] References Cited

U.S. PATENT DOCUMENTS

| | | | |
|---|---|---|---|
| D. 247,372 | 2/1978 | Whitehead | D24/51 |
| 2,392,695 | 1/1946 | Rohdin | 154/42 |
| 2,467,133 | 4/1949 | Irons | 154/126 |
| 2,599,359 | 6/1952 | Banks et al. | 154/139 |
| 2,614,953 | 10/1952 | Anglada | 154/42 |
| 3,315,676 | 4/1967 | Cooper | 128/287 |
| 3,369,547 | 2/1968 | Sack et al. | 128/296 |
| 3,442,268 | 5/1969 | Bird | 128/280 |
| 3,447,433 | 11/1969 | Dillon | 128/290 |
| 3,530,023 | 9/1970 | Schutte et al. | 156/290 |
| 3,562,041 | 2/1971 | Robertson | 156/73 |
| 3,661,665 | 5/1972 | Froget | 156/65 |
| 3,669,800 | 6/1972 | Gore | 156/383 |
| 3,688,771 | 9/1972 | Werner | 128/290 R |
| 3,733,238 | 5/1973 | Long et al. | 156/580 |
| 3,844,869 | 10/1974 | Rust, Jr. | 156/358 |
| 3,879,256 | 4/1975 | Rust, Jr. | 156/580 |
| 3,902,954 | 9/1975 | Lotto | 156/510 |

(List continued on next page.)

FOREIGN PATENT DOCUMENTS

0109924  5/1984  European Pat. Off. .
2540467  3/1977  Fed. Rep. of Germany .

Primary Examiner—James J. Bell
Attorney, Agent, or Firm—E. Kelly Linman; John V. Gorman; Richard C. Witte

[57] ABSTRACT

Method and apparatus for ultrasonically bonding continuously moving webs to one another using a stationary vibrating horn and a relatively slick, non-thermally softenable moving slip layer interposed between the webs to be bonded and the horn to prevent web damage. Interposing the slip layer between the webs to be bonded and the ultrasonic horn improves both the quality and efficiency of web bonding. It reduces friction between the travelling webs and the substantially stationary ultrasonic horn not only due to its relatively slick surface, but also due to the compressive force which the slip layer exerts upon the webs to be bonded. This in turn minimizes jamming and hangups in the very limited clearance existing between the rotating anvil roll and the substantially stationary vibrating ultrasonic horn. In addition, the slip layer maximizes retention of heat either generated in the laminate web by the ultrasonic horn or transferred to the laminate web structure by preheating one or more of the webs. If desired, the slip layer may be comprised of a continuous belt which rotates about the ultrasonic horn. In addition, a secondary slip layer may be provided intermediate the webs to be bonded and the rotating anvil roll to minimize heat transfer from the webs to the anvil roll and to prevent sticking of the webs to the anvil roll. In a particularly preferred embodiment the peripheral edges of the raised anvil bosses are relieved slightly to minimize web tearing and to enhance bond strength. In still another preferred embodiment the anvil roll is heated to a temperature approximating the maximum temperature achieved by the webs being bonded to minimize heat transfer from the webs to the anvil roll during the bonding operation. Novel laminate products bonded on-the-fly without the use of an ancillary adhesive may also be produced.

7 Claims, 6 Drawing Sheets

U.S. PATENT DOCUMENTS

| | | | |
|---|---|---|---|
| 3,929,135 | 12/1975 | Thompson | 128/287 |
| 3,966,519 | 6/1976 | Mitchell et al. | 428/296 |
| 3,982,991 | 9/1976 | Hamm et al. | 156/515 |
| 3,993,532 | 11/1976 | McDonald et al. | 156/580 |
| 4,146,416 | 3/1979 | Goldman | 156/580 |
| 4,256,529 | 3/1981 | Clarke et al. | 156/515 |
| 4,259,399 | 3/1981 | Hill | 428/288 |
| 4,300,562 | 11/1981 | Pieniak | 128/287 |
| 4,311,540 | 1/1982 | Hill | 156/73.1 |
| 4,321,924 | 3/1982 | Ahr | 128/287 |
| 4,323,068 | 4/1982 | Aziz | 128/287 |
| 4,323,069 | 4/1982 | Ahr et al. | 128/287 |
| 4,332,253 | 6/1982 | Schoots | 128/287 |
| 4,333,782 | 6/1982 | Pieniak | 156/164 |
| 4,342,314 | 8/1982 | Radel et al. | 128/287 |
| 4,353,762 | 10/1982 | Bouda | 156/164 |
| 4,395,215 | 7/1983 | Bishop | 425/290 |
| 4,397,645 | 8/1983 | Buell | 604/380 |
| 4,400,227 | 8/1983 | Riemersma | 156/73.1 |
| 4,404,052 | 9/1983 | Persson et al. | 156/73.1 |
| 4,407,284 | 10/1983 | Pieniak | 604/385 |
| 4,430,148 | 2/1984 | Schaefer | 156/580.2 |
| 4,463,045 | 7/1984 | Ahr et al. | 428/131 |
| 4,473,432 | 9/1984 | Leader et al. | 156/582 |
| 4,478,659 | 10/1984 | Hall | 156/73.1 |
| 4,498,946 | 2/1985 | Schöllkopf et al. | 156/324 |
| 4,519,798 | 5/1985 | Dinius | 604/358 |
| 4,543,154 | 9/1985 | Reiter | 156/73.1 |
| 4,572,753 | 2/1986 | Bach | 156/73.1 |
| 4,605,454 | 8/1986 | Savovitz et al. | 156/73.1 |
| 4,650,481 | 3/1987 | O'Connor et al. | 604/380 |

ADHESIVE-FREE BONDING OF CONTINUOUSLY MOVING WEBS TO FORM LAMINATE WEB AND PRODUCTS CUT THEREFROM

This is a division of application Ser. No. 835,068, filed on Feb. 28, 1986.

TECHNICAL FIELD

The present invention relates to method and apparatus for continuously bonding moving webs to one another without the use of an adhesive.

The present invention has further relation to such a method wherein at least one of the webs to be bonded is comprised of a polymeric material which can be locally melted or softened by the input of mechanical energy, whereby upon cooling and solidification of the melted or softened material said webs are securely bonded to one another.

The present invention has further relation to continuous method and apparatus for bonding one or more relatively delicate polymeric webs to one or more resilient highly compressible webs without damaging either said polymeric webs or said highly compressible webs.

The present invention has further relation to continuous method and apparatus for bonding one or more polymeric webs which can be locally melted or softened by the input of a given amount of mechanical energy to one or more webs which exhibits a significant interstitial void volume and which need not be locally melted or softened by the same input of mechanical energy.

The present invention has further relation to such a method wherein at least one of the elements used to input mechanical energy is substantially stationary in the direction of web travel and a moving slip layer which travels with the webs to be bonded is interposed between the group of webs to be bonded and the substantially stationary element used for inputting mechanical energy to the webs.

The present invention has further relation to such a method wherein the substantially stationary mechanical element comprises a vibrating ultrasonic horn and the moving slip layer minimizes friction between the webs and the substantially stationary mechanical element, thereby reducing the likelihood of damage to any of the webs during the bonding process.

The present invention has further relation to such an ultrasonic bonding method wherein the anvil roll employs a boss pattern which includes a shallow step or relief angle along its peripheral edge or edges to reduce the likelihood of web damage and to improve bond strength.

The present invention has further relation to an ultrasonic bonding method wherein all of the webs are bonded to one another, but the slip layer is not bonded to the resultant laminate structure.

The present invention has further relation to the use of such a moving slip layer to thermally insulate the webs being bonded from one or both of the mechanical elements used to input mechanical energy and thereby minimize heat loss via conduction from the heated polymeric material in the webs being bonded to the adjacent mechanical elements.

The present invention has further relation to the use of a moving slip layer of the aforementioned type which can also serve a utilitarian function in the resultant product such as the protection of a pressure sensitive adhesive used to secure the resultant product in place until such time as the end user is ready to place the product in service.

The present invention has further relation to the use of a continuous belt comprised of a suitable low friction, insulative material which moves with the travelling webs to be bonded as they pass between the mechanical elements used to input mechanical energy to the webs.

The present invention has further relation to the use of an ultrasonic bonding system employing a heated anvil roll to minimize the loss of heat from the webs being bonded to the anvil roll via conduction.

The present invention has still further relation to laminate structures which are bonded on-the-fly while the webs comprising the laminate structure are continuously moving in the machine direction, said laminate structures comprising a pair of polymeric webs which can be locally melted or softened by inputting mechanical energy thereto located adjacent at least one intermediate resilient, highly compressible web exhibiting a significant interstitial void volume, said polymeric webs and said intermediate web being secured to one another without the use of an ancillary adhesive by mechanical entanglement and/or fusion.

BACKGROUND INFORMATION

Methods of welding stacks of thermoplastic material to one another without the use of an ancillary adhesive material are generally known in the art. Heat sealing and ultrasonic bonding have often been used in such prior art processes. Many such prior art bonding processes are static, i.e., there is little or no lateral movement between the pieces being bonded and the bonding apparatus.

Typical of prior art processes which utilize heat to soften two or more polymeric layers and bond them to one another is U.S. Pat. No. 4,519,798 issued to Dinius on May 28, 1985. Dinius discloses a disposable diaper structure wherein an adsorbent core is encapsulated between a multiplicity of sheets. Each of the sheets is constructed of a material, such as polyethylene, which will heat seal without the necessity of an adhesive. The diaper is made by heating and sealing the overlapping edges of the polyethylene sheets directly to one another outside the borders of the absorbent core.

Representative of prior art continuous web bonding processes using ultrasonic bonding systems is U.S. Pat. No. 3,733,238 issued to Long et al. on May 15, 1973. Long et al. describe mechanism for producing laminated sheet materials and particularly for welding together layers of thermoplastic materials by the use of ultrasonic vibration equipment. A plurality of spaced ultrasonic vibration transmitting members having working surfaces in direct contact with one side of the sheet-like elements is employed in cooperation with opposing spaced anvil surfaces located on the opposite side of the sheet-like elements to produce full width webs of thermoplastic laminated material.

Commonly assigned U.S. Pat. No. 4,404,052 issued to Persson et al. on Sept. 13, 1983 also discloses prior art method and apparatus for continuously ultrasonically bonding together a plurality of juxtaposed webs to form a laminate structure as the webs are being driven forward at a relatively high velocity. Persson et al. teach that the regions of the webs to be bonded are subjected to progressively increasing compressive forces while simultaneously being subjected to ultrasonic energy as they traverse a portion of a predetermined path at a predetermined velocity.

Commonly assigned U.S. Pat. No. 4,430,148 issued to Schaefer on Feb. 7, 1984 discloses still another prior art continuous ultrasonic bonding system wherein a discrete pattern of protruberances is so configured and disposed on the anvil in its machine direction as to obviate cobblestoning of the transducer with respect to the anvil as a patterned portion thereof is moved past the transducer tip. The discrete pattern of protruberances is preferably so configured and disposed transverse the apparatus to precipitate wear preferably even wear—of the tip of the ultrasonic transducer of the apparatus along the entirety of a line-of-contact portion thereof.

Other exemplary ultrasonics bonding systems of the prior art are disclosed in U.S. Pat. No. 3,879,256—Russ; U.S. Pat. No. 3,993,532—McDonald et al; U.S. Pat. No. 4,146,416—Goldman; U.S. Pat. No. 4,311,540—Hill; and U.S. Pat. 3,562,041—Robertson. The latter reference discloses an ultrasonic laminating apparatus wherein the bonding pattern comprises a continuous line which closes upon itself.

While the prior art discloses method and apparatus which have been developed to overcome many of the problems of continuously bonding webs to one another on-the-fly without use of an ancillary adhesive, it is believed that the majority of these methods have been limited to situations wherein each of the webs to be bonded is capable of being locally melted or at least softened sufficiently to permit localized bonding.

Furthermore, the known prior art has not solved all of the problems associated with continuous on-the-fly adhesive-free web bonding or laminating operations. This is particularly true with respect to web bonding operations using one or more substantially stationary elements to input mechanical energy to the webs to effect bonding. In the case of ultrasonic bonding processes using a substantially stationary vibrating ultrasonic horn, web damage due to tearing, web damage due to web jamming, and web damage caused by sticking of the web or webs to the elements used to input mechanical energy are frequently experienced. These problems are generally more acute when one or more of the webs to be bonded is relatively weak, when one or more of the webs is highly compressible and/or when the incoming web speeds are very high. Furthermore, the known prior art systems do not exhibit an ability to concentrate and retain the heat generated in the web or webs to be bonded rather than being lost to the elements used to input the mechanical energy.

Accordingly, it is an object of the present invention to provide method and apparatus which will permit continuous, high speed, adhesive-free mechanical web bonding on-the-fly, i.e., while the webs are being forwarded in juxtaposed relation, without significant web damage.

It is another object of the present invention to provide continuous method and apparatus for bonding on-the-fly one or more webs which can be locally melted or softened by inputting a given amount of mechanical energy thereto to one or more webs which exhibit a significant interstitial void volume, but which need not be locally melted or softened by the input of the same amount of mechanical energy, all without damaging any of said webs.

It is another object of the present invention to provide continuous method and apparatus for bonding on-the-fly one or more locally meltable or softenable polymeric webs to one or more resilient, highly compressible webs without damaging any of said webs.

It is another object of the present invention to provide continuous web bonding method and apparatus wherein most of the heat inputted to or generated in the webs being bonded is concentrated and retained in the webs rather than being lost via conduction to the mechanical elements utilized to input energy to the webs.

It is another object of the present invention to provide a laminate structure which is bonded on-the-fly without the use of an ancillary adhesive, said laminate structure comprising a pair of locally meltable polymeric webs located adjacent the outermost surfaces of a resilient, highly compressible web exhibiting a significant void volume, said polymeric webs being bonded to said compressible web by mechanical entanglement with the compressible web as well as to one another through the interstices comprising the void volume in said compressible web.

It is still another object of the present invention to provide the aforementioned benefits in a simple yet effective manner which does not significantly increase the cost of the resultant laminate product.

DISCLOSURE OF THE INVENTION

In a particularly preferred embodiment, the present invention employs a moving slip layer between at least one of the exterior webs to be bonded and the adjacent mechanical element used for inputting mechanical energy to the webs, said slip/layer travelling with the webs during the bonding process to minimize friction between the webs and the mechanical element in question. Although the webs are bonded to one another by the input of mechanical energy, the slip layer is not bonded to the resultant laminate structure. The slip layer not only minimizes the chance of damage to the relatively fragile webs during the bonding process, but in addition helps to insulate the webs from the mechanical element or elements used to input energy. The avoidance of web damage is most pronounced in situations where at least one of the webs to be bonded is highly compressible and resilient, while the insulative effect minimizes heat loss via conduction from the heated polymeric material being bonded to the mechanical element in question. This may be of particular value in ultrasonics bonding operations which are followed by an additional compression step before the laminate structure has cooled, since it retains the heat in the webs for a longer period of time. The slip layer also prevents sticking of the webs to the mechanical elements.

In a particularly preferred embodiment, the slip layer can also serve a utilitarian function in the resultant product, e.g., the protection of a pressure sensitive adhesive used to secure the resultant laminate product in place until such time as the end user is ready to place the product in service.

As will be apparent from the foregoing, the slip layer of the present invention is not permanently bonded to the remainder of the webs comprising the resultant laminate. Accordingly, it may be removed immediately after the web bonding process has been completed or it may remain with the resultant products cut from the laminate web.

In another preferred embodiment of the present invention, the slip layer comprises a continuous belt which rotates continuously about the mechanical energy inputting element in question, preferably at the same speed as the incoming webs. If desired, a pair of such belts or a pair of slip layers may be employed in web bonding operations of the present invention, one between each mechanical element and the adjacent surface of the group of webs to be bonded to one another.

In another preferred embodiment of the present invention the mechanical energy inputting elements comprise a vibrating ultrasonic horn and an anvil roll having a pattern of raised bosses which are relieved slightly along their peripheral edges to minimize web damage and enhance bond strength.

In still another preferred embodiment the anvil roll is heated to a temperature approximating the maximum temperature exhibited by the webs during the bonding process to minimize heat transfer from the webs being bonded to the anvil roll during the bonding operation.

While the present invention can be practiced to advantage at low web bonding speeds, its advantages become most pronounced at high web bonding speeds, e.g., speeds in excess of about 200 feet per minute. Even bulky, yet fragile materials can be bonded without significant damage to the webs and without any significant increase in the cost of the resultant laminated product. In addition it facilitates production of novel laminate structures wherein one or more polymeric webs which can be locally melted or softened by the input of a given amount of mechanical energy can be bonded to one or more webs which need not be locally melted or softened by the same input of mechanical energy to form a laminate structure without the use of an ancillary adhesive.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE INVENTION

Figure 1:
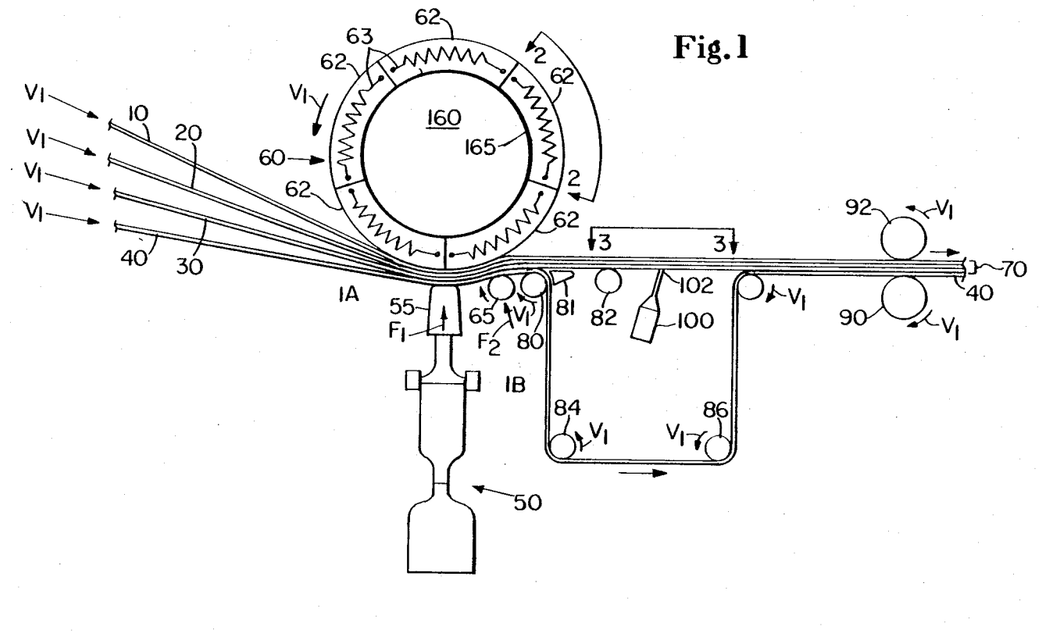
FIG. 1 is a simplified schematic illustration of a preferred process of the present invention.

FIG. 1 discloses a preferred embodiment of the present invention. In particular, a multiplicity of moving webs 10, 20 and 30 to be bonded to one another are fed at the same incoming velocity $V_1$ between the contact surface 56 of a substantially stationary vibrating ultrasonic horn 55 and an anvil roll 60, which also rotates at a peripheral velocity $V_1$. As the webs pass between the vibrating ultrasonic horn 55 and rotating anvil roll 60, they are bonded to one another in a predetermined pattern. An intermediate layer 40, which in the illustrated embodiment comprises a relatively slick feeling, silicone impregnated release paper is interposed between the lowermost surface of web 30 and the relatively smooth surface 56 of ultrasonic horn 55.

As can be readily observed from FIG. 1, the layer of release paper 40 is not permanently joined to the other webs during the bonding process.

In the embodiment disclosed in FIG. 1, the process is utilized to make a web of interconnected absorptive bandages 310 which may therafter be cut into discrete products useful as sanitary napkins, panty liners or the like. Accordingly, the uppermost or body contacting web 10 is preferably comprised of a body fluid-pervious material. Conventional materials such as heat softenable, non-woven polymeric webs may, if desired, be used for this purpose.

An alternative fluid-pervious material comprised of resilient, macroscopically expanded, apertured, three-dimensional polymeric film is disclosed in commonly assigned U.S. Pat. No. 3,929,135 issued to Thompson on Dec. 30, 1975. The Thompson patent describes a permeable topsheet comprised of heat softenable polymeric film provided with tapered capillaries of conical construction.

Still another suitable material for web 10 which is particularly preferred in situations where the absorbent bandage is used as a sanitary napkin or panty liner is disclosed in commonly assigned U.S. Pat. No. 4,342,314 issued to Radel et al. on Aug. 3, 1982, which is hereby incorporated herein by reference. Radel et al. disclose a resilient, macroscopically expanded, apertured three-dimensional, heat softenable polymeric web exhibiting a fiber-like appearance and tactile impression. In a particularly preferred embodiment, the web exhibits a regulated continuum of three-dimensional debossed areas. The debossed areas preferably comprise apertured capillary networks interconnecting the first and second surfaces of the web. The networks are preferably of decreasing size in the direction of the second surface of the web to promote fluid transport from the first surface of the web to the second surface of the web and inhibit the flow of fluid in the reverse direction.

In the embodiment illustrated in FIG. 1, web 20 is preferably comprised of some type of high loft, preferably resilient, absorbent material exhibiting significant void volume to absorb and retain fluids initially deposited on the uppermost fluid-pervious body contacting web 10 and thereafter transmitted to absorbent web 20. As a practical matter, web 20 is often comprised of multiple layers of material which, together, provide desirable wicking and fluid retention characteristics. For example, web 20 may be comprised of a multiplicity of tissue plies, a polyester batt having an absorbent tissue ply adjacent one or both surfaces thereof or the like.

It is, of course, recognized that it is possible to form laminate structures wherein one or more layers may be of lesser width than the layers being bonded to another. In the latter case, the layer or layers of lesser width may be encapsulated between the bonded layers without the necessity of bonding all the way through the encapsulated layer or layers about the entire perimeter of the laminate structure.

It is also recognized that the nature of the bond formed between the heat softenable polymeric webs and the other layers in the structure will vary, depending upon the characteristics of the other layers. For example, if all of the layers are comprised of polymeric materials which are softenable by inputting a given quantity of mechanical energy and which are compatible with one another from the standpoint of sealing, all of the layers will be fused to one another. On the other hand, if one or more of the layers is not softenable by the input of the same amount of mechanical energy but nonetheless exhibits a significant interstitial void volume, the bonding will likely comprise mechanical entanglement of the melted or softened polymeric materials with the non-softenable web or webs and/or fusing of the polymeric webs to one another through the interstitial void volume in the non-softenable web or webs. Thus, the particular choice of material for absorbent web 20 is non-critical to the practice of the present invention, provided the material or materials chosen will permit at least one of the aforementioned forms of bonding to occur between the various layers comprising the laminate. As will be appreciated from the foregoing comments, it is not essential that web 20 be comprised of a material which is locally meltable or softenable by the input of thermal or mechanical energy.

Web 30, on the other hand, is preferably comprised of a substantially fluid-impervious material to prevent body fluids absorbed by absorbent web 20 from penetrating the outermost surface of the absorbent structure and causing soiling of the wearer's garments. A single ply of heat softenable polymeric material such as polyethylene film having a thickness on the order of about 1 mil (0.001 inches) normally serves well in this regard.

Alternatively, web 30 could be comprised of a resilient, macroscopically expanded, three-dimensional, heat softenable polymeric web exhibiting a multiplicity of debossments which are unapertured to provide desirable visual and tactile impression on the non-wearer contacting surface of the resultant bandage, yet resist penetration by the absorbed fluids. Materials of the latter type are also disclosed in commonly assigned U.S. Pat. No. 4,342,314 issued to Radel et al. on Aug. 3, 1982, which is incorporated herein by reference. In this regard, particular attention is directed to the web embodiment shown in FIG. 6D of the aforementioned Radel et al. patent. If desired, this embodiment of the Radel et al. web can be made to exhibit substantially the same three-dimensional appearance and tactile impression as fluid-pervious web 10, while remaining unapertured and hence fluid-impervious.

As defined herein, heat softenable polymeric webs, such as webs 10 and 30, are those which have a softening temperature and which can be locally melted or softened by the input of mechanical energy thereto.

Figure 1A:
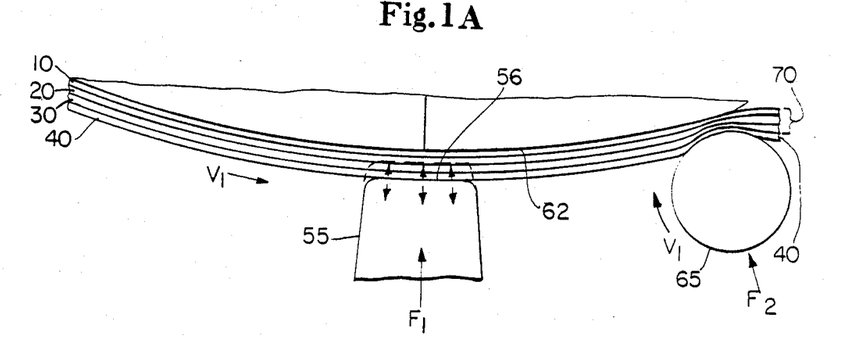
FIG. 1A is a greatly enlarged view of inset 1A shown in FIG. 1.

As can be seen in FIG. 1, bonding of webs 10, 20 and 30 to one another is carried out without the addition of an adhesive material by simultaneously passing these webs along with an insulative slip layer 40 at the same velocityh $V_1$ between a substantially stationary ultrasonic bonding apparatus indicated generally at 50 and an anvil roll 60, which rotates at a peripheral velocity $V_1$ equal to that of the incoming webs. The ultrasonic bonding apparatus is normally pneumatically or hydraulically loaded by means of a cylinder and linkage arrangement (not shown) so as to exert a substantially constant force $F_1$, which translates to a substantially constant pressure on the webs passing between the vibrating horn 55 of the ultrasonic bonding apparatus and anvil roll 62. Although the ultrasonic horn 55 remains substantially stationary relative to the direction of travel of the webs, the inset of FIG. 1A shows that the horn 55 actually vibrates at ultrasonic frequency in a direction substantially perpendicular to the surface of the webs. The exterior, i.e., lowermost, surface of the insulative slip layer 40 contacts the surface 56 of the substantially stationary, vibrating ultrasonic horn 55 during the bonding process. The forces exerted on the web by the vibrating ultrasonic horn 55 are resisted by the anvil roll 60 which preferably includes a multiplicity of platens indicated generally at 62 mounted about its periphery. The raised pattern on each platen 62 is shown in enlarged form in FIG. 2, which is taken along view line 2—2 of FIG. 1.

Figure 2:
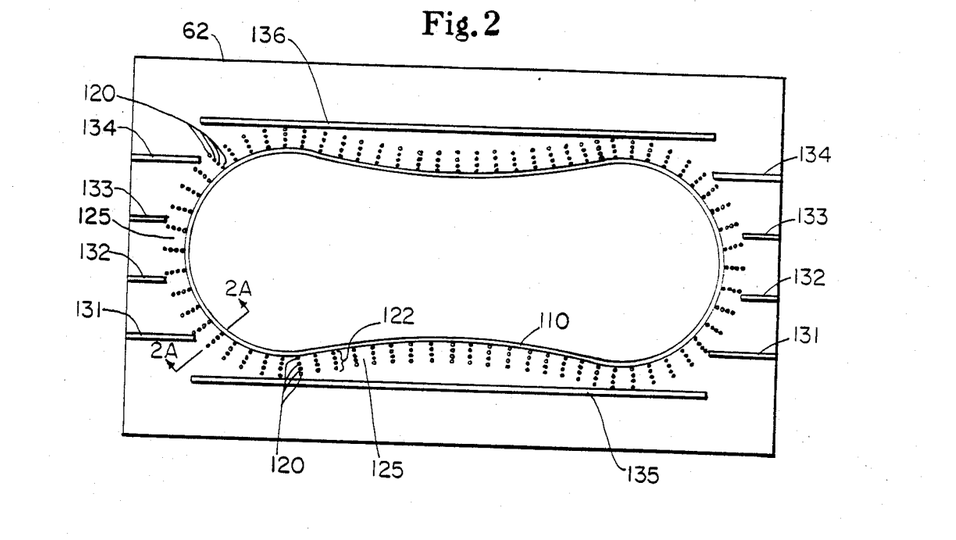
FIG. 2 is a greatly enlarged simplified view of a surface portion of the anvil roll taken along view line 2—2 of FIG. 1.

For the embodiment disclosed in FIGS. 1 and 2, each platen 62 includes a continuous hourglass-shaped raised boss 110 which outlines the area for which a continuous seal is desired between webs 10, 20 and 30. A multiplicity of small, discrete raised bosses 120 oriented so as to form discontinuous lines 122 spaced apart from one another and oriented substantially perpendicular to the continuous, hourglass-shaped boss 110 are preferably provided about the entire periphery of the continuous boss 110. Intermediate each pair of lines 122 of discrete bosses 120 is an unobstructed area 125 which is preferably free of bosses to provide a spaced apart sealing pattern about the periphery of continuous boss 110.

Figure 2A:
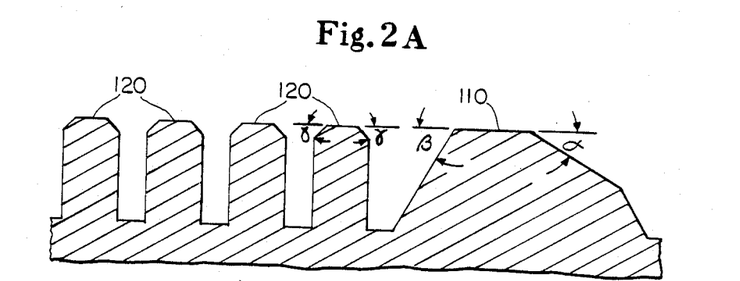
FIG. 2A is a greatly enlarged cross-section of the anvil roll's raised boss pattern taken along section line 2A—2A of FIG. 2.

The greatly enlarged cross-section of FIG. 2A illustrates a particularly preferred profiling for the continuous boss 110 and the discrete raised bosses 120. In particular, it has been determined that elimination of sharp square corners on the raised bosses not only reduces web tearing, but in addition, provides improved seal strength. In particular, it is believed that providing the edges of the bosses 110 and 120 with a profile having a relief angle such as $\alpha$, $\beta$ or $\gamma$ between about 15° and about 45°, provides a gradual transition from intense energy and pressure input at the top of the boss to a lower energy and pressure level at its peripheral edges. Experience has demonstrated that such profiling of the peripheral edges of the bosses actually broadens the resultant bond area. Bonds produced with such profiled bosses exhibit better strength than bonds produced utilizing similar bosses having unprofiled rectangular edges. Although the benefits of profiling the bosses are apparent when ultrasonically bonding as few as two layers to one another whether or not an insulative slip layer such as 40 is employed, these benefits, particularly the damage reduction benefit, are particularly pronounced when one or more of the layers to be bonded is resiliently compressible. Benefits afforded by the profiled bosses are also more pronounced at higher web speeds.

For most efficient operation, it is generally desirable that the contact area presented by the anvil roll 60 remain essentially constant across the substantially smooth surface 56 of ultrasonic horn 55. This avoids the need for cycling the ultrasonic horn 55 on and off intermediate adjacent products being formed in the laminate web. In addition it avoids the generation of pressure loads of continuously varying magnitude between the vibrating ultrasonic horn 55 and the anvil roll 60. This not only makes tuning the system to optimize web bond strength and quality easier, but also substantially eliminates cyclic loading of the ultrasonic bonding equipment, which is believed to have a beneficial effect on equipment life.

In the embodiment shown in FIG. 2, substantially constant pressure loading between the ultrasonic horn 55 and each platen 62 on the rotating anvil roll 60 is preferably accomplished by providing raised bosses 131, 132, 133 and 134 in those areas of the platen 62 located intermediate adjacent products to be formed in the laminate web.

In the embodiment of the present invention illustrated in FIG. 1 the pressure loading of horn 55 is preferably adjusted to provide a pressure in the range of about 400 to about 1,500 pounds per square inch, as measured at the boss pattern on each platen 62.

As can be seen in FIG. 2, the total contact area represented by continuous hourglass-shaped boss 110 and the multiplicity of small discrete bosses 120 configured as discontinuous lines 122 about its periphery will not be constant at all points along the web's traverse of the contact surface 56 of ultrasonic horn 55, as measured in the machine direction. To compensate for this, raised bosses 135 and 136 are preferably employed adjacent each continuous raised boss 110 to bring the total anvil contact area to a substantially constant value at all points along platen 62 as the webs traverse the surface 56 of vibrating ultrasonic horn 55. As will be appreciated by those skilled in the art, relieving the peripheral edges of the raised bosses via profiling, as generally shown in FIG. 2A, effectively reduces the contact area of the raised bosses. Accordingly, the cross-sectional area calculations to accomplish the foregoing objective are preferably based only on those raised boss surfaces which remain substantially parallel to the axis of rotation of the anvil roll. As will also be appreciated by those skilled in the art, the degree of machine direction overlap between raised bosses 135 and 136 relative to raised bosses 131, 132, 133 and 134 will depend upon the size and configuration of the bonding pattern to be imparted to the product or products being formed in the web as well as the area of horn surface 56.

While not wishing to be bound, it is believed that the insulative slip layer 40 of the present invention which passes adjacent surface 56 of the substantially stationary, vibrating ultrasonic horn 55 improves the quality and efficiency of web bonding in two important respects. First, it reduces friction between the travelling webs and the substantially stationary, vibrating ultrasonic horn 55. This is accomplished not only by the relative slickness of the web 40, which may comprise a simple silicone impregnated paper, but also by the compressive force which web 40 exerts on webs 10, 20 and 30 prior to entry of the assemblage into the very limited clearance existing between the rotating anvil roll 60 and the leading edge of the substantially stationary, vibrating ultrasonic horn 55. Note that sharp edges are also avoided at the leading edge of ultrasonic horn 55 to minimize the possibility of damaging the incoming webs and slip sheet as the vibrating horn moves in the direction of anvil roll 60.

As can be seen in FIGS. 1 and 1A, increasing the tension in web 40 will tend to squeeze webs 10, 20 and 30 more tightly against anvil roll 60, thereby reducing their overall thickness prior to encountering the leading edge of the continuously vibrating ultrasonic horn 55. This not only reduces the friction force exerted against the relatively smooth surface 56 of ultrasonic horn 55 by the webs, but also reduces the chance of web jamming and consequent web damage which may otherwise occur at the leading edge of ultrasonic horn 55. In addition, because the ultrasonic horn vibrates continuously at high frequency in a direction substantially perpendicular to slip layer 40, as shown in the greatly enlarged inset of FIG. 1A, it is believed that the presence of slip layer 40 reduces the severity of the shock load transmitted to webs 10, 20 and 30 each time the horn moves toward anvil roll 60. In particular, it is believed that some slippage occurs between the surface of slip layer 40 in contact with surface 56 of vibrating horn 55 and some slippage occurs between the surface of slip layer 40 in contact with web 30. This in turn reduces the severity of the shearing action induced in webs 10, 20 and 30 as the moving webs attempt to pass the substantially stationary, vibrating horn 55 to a level which avoids damage to the webs, yet which is sufficient for the polymeric webs 10 and 30 to become locally melted or at least softened. Use of insulative slip layer 40 thus permits non-destructive inputting of sufficient mechanical energy to facilitate localized melting of softening of polymeric layers 10 and 30 so that they may bond not only to the intermediate absorbent web 20 by entanglement, but also to one another through any interstitial void spaces existing in absorbent web 20.

In the event intermediate absorbent web 20 is also softenable by the same input of mechanical energy required to soften the adjacent webs 10 and 30, then the resultant bond between intermediate layer 20 and layers 10 and 30 will involve not only mechanical entanglement, but also a degree of fusion. In some instances involving intermediate webs comprised of polyester batt or the like, which typically do not soften as quickly as adjacent webs comprised of materials such as polyethylene, binders or resins having a lower softening point are often applied. These binders which impart mechanical integrity to the polyester batt have been found to soften during the bonding process. As a result they contribute to the resultant bond strength of the laminate structure even though the polyester filaments to which the binder is applied do not actually undergo softening.

It is also recognized that when intermediate layer 20 is comprised of multiple plies, the type of bonding present across the thickness of the laminate structure may vary from layer to layer. For example, if layer 20 is comprised of a layer of binder treated polyester batting having a tissue ply adjacent its uppermost surface, the uppermost heat softenable polymeric layer 10 may become mechanically entangled in the interstitial void volume of the tissue ply. Similarly the heat softenable binder on the polyester batting and the material comprising lowermost heat softenable polymeric layer 30 may secure layer 30 and the batting to one another by a combination of fusion and mechanical entanglement. In addition, layer 30 and the polyester batting may be secured to the interstitial void volume of the tissue ply by mechanical entanglement. As a result the entire structure is bonded together to form a laminate, but the nature of the bond varies between the various layers.

Whatever the nature of the resultant bonding mechanism, it has generally been observed that when insulative slip layer 40 is not present, severe web damage often results when attempts are made to bond on-the-fly one or more locally meltable or softenable polymeric webs to one or more resilient, highly compressible webs by the input of mechanical energy through a substantially stationary, vibrating ultrasonic horn.

In practicing the present invention it has generally been found desirable to retain any heat either added to the laminate web structure by preheating or generated in the laminate web structure by the mechanical action of ultrasonic horn 55. Preheating of one or more of the webs is preferably accomplished by directing hot air blasts or the like (not shown) at the web or webs in question at a point upstream of the ultrasonic bonding apparatus.

Alternatively or in addition to preheating of the webs, it has been found desirable to minimize loss of heat from the webs being bonded to the adjacent anvil roll 60 by preheating the anvil roll 62 to a temperature approximating the maximum temperature achieved by the webs during the bonding operation. This is accomplished in the embodiment of FIG. 1 by embedding electrical resistance heaters 63 or the like in platens 62. In a particularly preferred embodiment a layer of insulative material 165 is installed between the platens 62 and the anvil roll hub 160 to minimize heat loss from the platens to the hub and thereby minimize warm-up time. Heating the anvil roll in this manner substantially eliminates any temperature differential between anvil roll 60 and the webs being bonded. As a result there is little or no heat transfer from the webs to the anvil roll during the bonding operation. It should be noted that such heating of the anvil roll to a temperature approximating the maximum temperature achieved by the webs being bonded has proven to be beneficial whether or not an insulative slip layer 40 is employed between the webs being bonded and the vibrating ultrasonic horn 55.

The insulative effect provided by slip layer 40 also prevents loss of the heat contained in the webs to the contact surface 56 of the vibrating ultrasonic horn 55. This is particularly important at high web speeds, since retention of heat in the area of the webs to be bonded enhances both bonding efficiency and quality. In addition, the insulative slip layer prevents sticking between the webs being bonded and the adjacent mechanical energy inputting element.

In the embodiment illustrated in FIG. 1, the ultrasonic bonding process is immediately followed by a pressure roll 65 which exerts a substantially constant force $F_2$ against all of the webs passing through the nip formed with anvil roll 60 before the ultrasonically bonded areas have cooled and set. If desired, the pressure roll can be operated against fixed stops which provide a minimum predetermined clearance with the anvil roll. In this case the pressure roll is preferably loaded with a constant force against the fixed stops which is sufficient to prevent the laminate web from lifting the pressure roll off the fixed stops. Pressure roll 65 helps to further improve both bond quality and strength, as described more completely in commonly assigned U.S. Pat. No. 4,400,227 issued to Riemersma on Aug. 23, 1983, which is hereby incorporated herein by reference.

From the foregoing description it will be appreciated that use of the insulative slip layer 40 generally produces greater benefits as the web bonding speed increases, i.e., although benefits are noticeable at web bonding speeds of about 100 feet per minute, they are most pronounced at web bonding speeds of about 200 feet per minute or greater. Furthermore, the beneficial reduction in damage to relatively delicate webs is most apprent when one or more of the webs to be bonded is highly compressible and resilient, since it is normally difficult to ultrasonically bond such webs to one another at high speed without damage.

As will be appreciated by those skilled in the art, the use of an additional insulative slip layer 40 which serves no purpose other than to increase bonding efficiency and quality would, in most instances, increase the cost of the resultant product made. However, if insulative slip layer 40 can be made to serve another required or desirable function in the resultant product, the use of web 40 to enhance bonding need not significantly increase the cost of the resultant laminate product.

In the case of a sanitary napkin, such as that disclosed herein, it is normally desirable to include securement means by which the resultant laminate article is maintained in position inside the user's undergarments. Typically, this securement means comprises one or more strips of pressure sensitive adhesive applied to the non-wearer contacting surface of the resultant product.

Figure 1B:
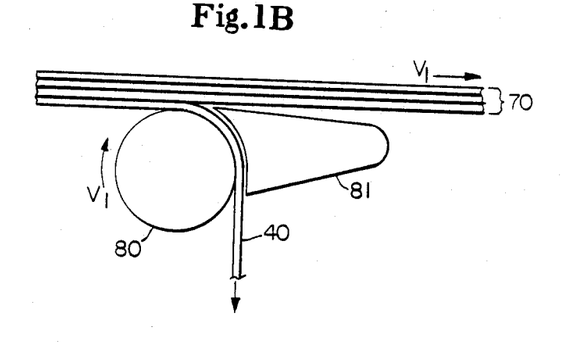
FIG. 1B is a greatly enlarged view of inset 1B shown in FIG. 1.

In the embodiment shown in FIG. 1, insulative slip layer 40, which is comprised of a relatively slick material which is not meltable or softenable by the input of mechanical energy, is not bonded to the remainder of the webs during the ultrasonic bonding process. Rather, it is preferably separated from the bonded web assemblage (identified as 70 after bonding) after it passes pressure roll 65. A plow 81 and idler rolls 80, 82 may be used to redirect the insulative slip layer 40, which is not bonded to the laminate assemblage 70, away from the assemblage 70. Separation of insulative slip layer 40 from the assemblage 70 is shown in the greatly enlarged inset of FIG. 1B. Once insulative slip layer 40 has been redirected downwardly, the bonded assemblage 70 passes over an adhesive applicator 100 which preferably applies one or more strips of pressure sensitive adhesive indicated generally ato 102 to the lowermost surface of the bonded assemblage 70. The insulative slip layer 40 is preferably fed about idler rolls 84, 86 and 88, as generally indicated in FIG. 1, so as to provide operating room for the pressure sensitive adhesive applicator 100. After passage over idler roll 88, insulative slip layer 40 is preferably recombined with the bonded web assemblage 70 by bringing it into contact with the pressure sensitive adhesive 102, as generally shown in FIG. 1. Since the insulative slip layer 40 continues to travel at the same velocity $V_1$ as the web assemblage 70, insulative slip layer 40 can readily be recombined with the bonded web assemblage 70 having one or more strips of pressure sensitive adhesive 102 on its lowermost surface by passing them between a pair of pressure rolls 90, 92. The pressure sensitive adhesive 102 secures the slip layer 40 to the bonded web assemblage 70 throughout any remaining processing operations, including the cutting (not shown) of discrete laminated products from the continuous web. Because of the relatively slick nature of slip layer 40, it can easily be removed by peeling it from the pressure sensitive adhesive 102 whenever the consumer is ready to place the product in service.

As an alternative to the process illustrated in FIG. 1, it is believed that the pressure sensitive adhesive 102 could be applied to the lowermost surface of web 30 prior to carrying out the web bonding process disclosed in FIG. 1. In this case, the insulative slip layer 40 would remain secured to the resultant laminate web 70 until such time as the consumer was ready to place the discrete products cut from the laminate web into service.

Figure 3:
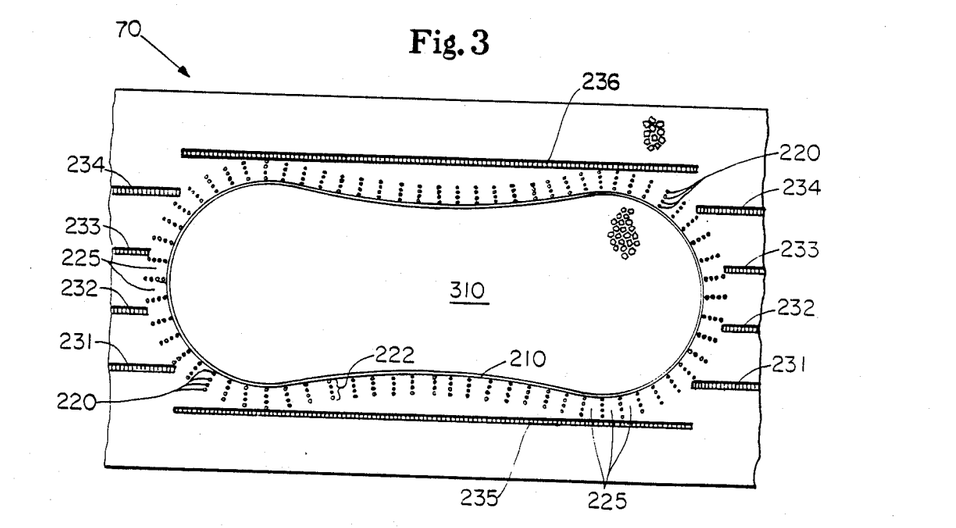
FIG. 3 is a greatly enlarged view taken along view line 3—3 of FIG. 1 showing the resultant pattern of bonding which occurs in the laminated web assembly as a result of passage between the ultrasonic horn and the anvil roll and the pressure roll shown in FIG. 1.

The pattern of bonding exhibited between webs 10, 20 and 30 of the assemblage 70 is generally shown in enlarged form in FIG. 3, which is taken along view line 3—3 of FIG. 1. As will be appreciated, the bonding configuration illustrated in the web assemblage 70 corresponds essentially to the pattern of raised bosses exhibited by each anvil roll platen 62, as generally shown in FIG. 2. Continuous hourglass-shaped seal 210 corresponds essentially to continuous hourglass-shaped raised boss 110; lines 222 of small discrete bonds 220 correspond essentially to lines 122 of discrete bosses 120; seals 231, 232, 233 and 234 intermediate adjacent products correspond essentially to raised bosses 131, 132, 133, and 134 respectively, of FIG. 2 and seals 235 and 236 correspond to raised bosses 135 and 136, respectively, of FIG. 2.

In a particularly preferred embodiment of the present invention, discrete, hourglass-shaped sanitary napkins 310 are cut from the bonded web assemblage 70 by severing them along a continuous line located outboard of continuous seal 210, but inboard of the outermost small, discrete seals 220 comprising discontinuous lines 222. This provides a pattern of unbonded areas 225 located intermediate each pair of discontinuous lines 222 of small, discrete seals 220. Because areas 225 are unbonded, they tend to resume the undeformed, no-load thickness of the resiliently compressible web 20, thereby providing a very soft feeling periphery about the absorbent bandage 310 cut from the bonded web assemblage. Meanwhile, the substantially continuous hour-glass shaped seal 210 minimizes the possible loss of absorbed fluid through the severed edges of the bandage in unbonded areas 225. If heat-softenable polymeric web 30 is fluid-impervious and coextensive in width to the finished sanitary napkin 310, a substantially fluid impermeable barrier will also be established along the lowermost surface of the sanitary napkin.

Figure 6:
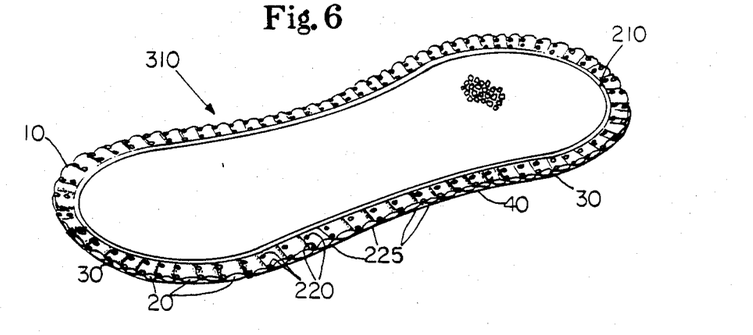
FIG. 6 is a simplified perspective illustration of an absorbent bandage cut from the resultant web assemblage shown in FIG. 1.

FIG. 6 is a simplified perspective illustration showing the resultant bandage 310 after it is cut from the bonded web assemblage 70.

Figure 4:
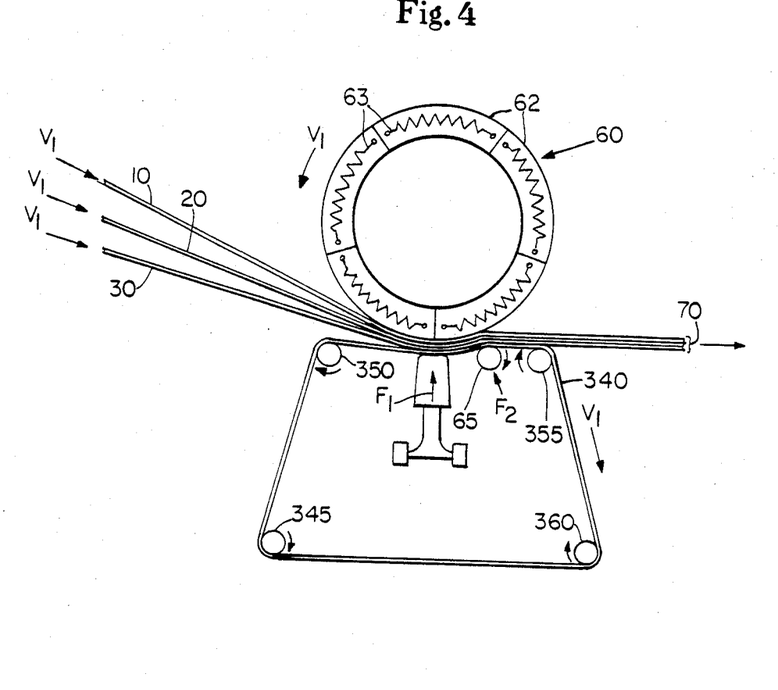
FIG. 4 is a simplified schematic illustration of an alternative bonding process of the present invention.

FIG. 4 discloses another simplified process embodiment of the present invention wherein a bonding system generally similar to that illustrated in FIG. 1 is employed to carry out an adhesive-free bonding process. However, in the embodiment shown in FIG. 4, insulative web 40 has been eliminated. In its place, a continuous insulative belt 340 operates at the same velocity $V_1$ as incoming webs 10, 20 and 30 about a multiplicity of rollers, 345, 350, 355 and 360, only one of which need be driven. A process configuration such as that generally shown in FIG. 4 is normally preferred in those situations where the resultant laminate product does not require an ancillary element which can also serve as the insulative slip layer. Continuously circulating a friction reducing, heat insulative belt, such as 340, across the surface 56 of the substantially stationary, vibrating ultrasonic horn 55 accomplishes substantially the same result as insulative slip layer 40 in the process embodiment shown in FIG. 1. However, it does not involve the additional expense associated with using and disposing of insulative slip layer 40 after a single pass between the stationary, vibrating horn 55 and anvil roll 60.

Figure 5:
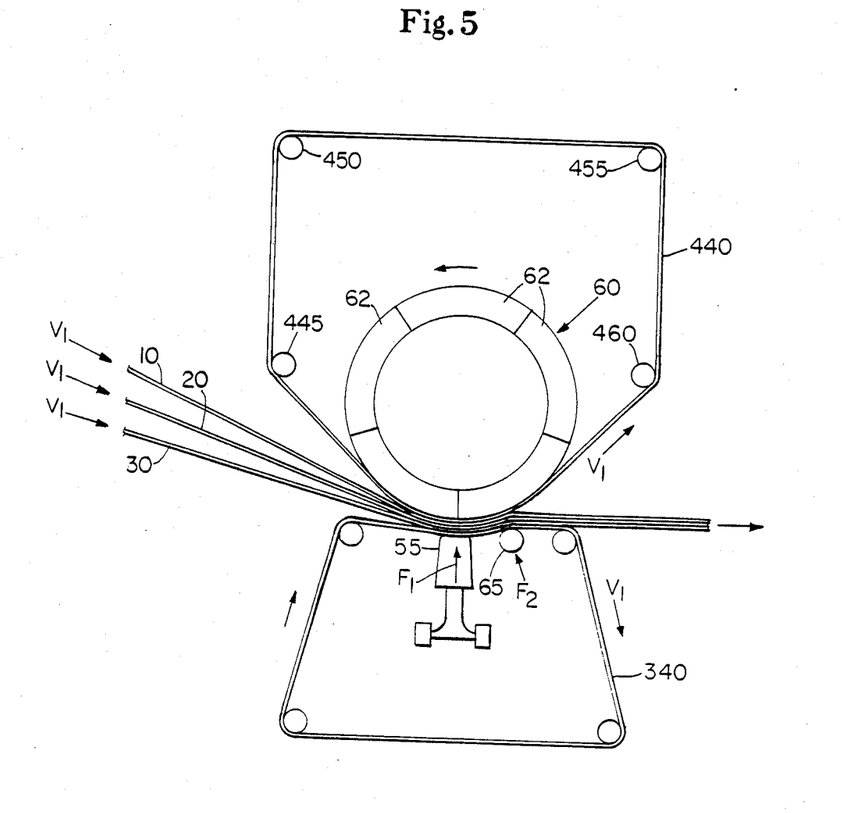
FIG. 5 is a simplified schematic illustration of still another bonding process of the present invention.

As pointed out earlier herein, if it is desired to maximize the insulative effect of the slip layer, it may in certain instances be desirable to provide such a layer between the webs to be bonded to one another and both of the mechanical elements used to input energy to the webs. The embodiment shown in FIG. 5 is generally similar to that of FIG. 4, with the exception that it includes a second continuous insulative belt 440 operating about anvil roll 62 and pulleys 445, 450, 455 and 460, only one of which need be driven. As with the embodiment of FIG. 4, belt 440 is preferably driven at the same velocity $V_1$ as the incoming webs 10, 20, and 30. However, in the embodiment of FIG. 5, the electrical resistance heaters 63 are not employed in the platens 62 of anvil roll 60, since the presence of insulative belt 440 would minimize any transfer of heat from the webs being bonded to the anvil roll platens 62. In this embodiment it is generally preferred that the webs themselves be preheated, as by means of hot air blasts (not shown) prior to their passage between the vibrating ultrasonic horn 55 and anvil roll 60. Since anvil roll 62 also rotates at a peripheral velocity $V_1$, substantially equal to that of the incoming webs, the primary benefit afforded by insulative belt 440 is to retain heat initially inputted to the webs or generated within the webs by the mechanical action of ultrasonic horn 55 rather than to reduce friction with the anvil roll. An additional benefit afforded by belt 440 is that it prevents sticking between the webs being bonded and anvil roll 60.

It is of course recognized that a continuous insulative layer similar to web 40 could be provided intermediate anvil roll 62 and uppermost web 10 in lieu of the continuously recirculating insulative belt 440. However, it is believed that the latter approach would generally be preferred only in the event such a web is required to perform some utilitarian function in the resultant product.

EXEMPLARY EMBODIMENT

An exemplary embodiment of an absorbent structure comprising a sanitary napkin of the type generally disclosed in connection with FIG. 1 was fabricated as follows:

A one mil thick fluid permeable polyethylene web of the type generally disclosed in commonly assigned U.S. Pat. No. 4,342,314 issued to Radel et al. on Aug. 3, 1982 and incorporated herein by reference was employed as the uppermost anvil roll contacting web corresponding to web 10 in the embodiment disclosed in FIG. 1. Directly beneath the uppermost web there was provided a web of tissue paper having a basis weight of 15 pounds per 3,000 square feet. Beneath the tissue paper web there was provided a web comprised of 100% polyester batting having a basis weight of three ounces per square yard. The batting was treated with a 12-15% (by weight) applicationof Acrylic Latex Binder Number E21-14NS, as available from Rohm & Haas Company of Philadelphia, Pa. to impart mechanical integrity. Together, the tissue web and the resin treated polyester batting web comprised the absorbent structure corresponding generally to web 20 in the embodiment disclosed in FIG. 1. Beneath the binder or resin treated polyester batting web there was provided a substantially planar, fluid impermeable barrier web comprised of one mil thick polyethylene. The latter web corresponds generally to fluid impermeable web 30 shown in the embodiment disclosed in FIG. 1. To improve the tactile impression of the outermost surface of the resultant product there was also provided beneath the one mil thick barrier layer of polyethylene a polypropylene nonwoven web comprised of Celestra ®, a registered trademark of Crown Zellerback Corporation of San Francisco, Calif., having a basis weight of 0.55 ounces per square yard. (This latter web has no correspondence to any of the webs disclosed in FIG. 1, and details of its use are included in this Example for completeness of description only.) Finally, the lowermost ultrasonic horn contacting slip layer, corresponding to slip layer 40 in FIG. 1, was comprised of silicone impregnated release paper having a basis weight of 31.5 pounds per 3,000 square feet and a machine direction tensile strength of 9,000 grams per inch of width.

A bonding apparatus generally similar to that shown in FIG. 1 was employed to bond the web assemblage together without permanently securing the release paper web to the assemblage. The ultrasonic bonding system comprised a Model 188P, as available from Branson Sonic Power Company of Danbury, Conn., said system being operated at a frequency of 20 kiloherz and drawing approximately 40% power. The ultrasonic horn was a Model No. 403-007-020 applied with a force $F_1$ sufficient to provide 650 psig loading against the raised bosses on the anvil roll platens. The horn was vibrated at an amplitude of approximately 2.9 mils, peak-to-peak. The horn stack included a Model No. 101-149-042 Booster installed between the horn and the converter. The temperature of the platens on the anvil roll was maintained at approximately 190° F. by the electrical resistance heaters embedded in each of the platens. The assemblage of webs, including the release paper used as a slip/layer were passed between the vibrating ultrasonic horn and the anvil roll at a web speed of approximately 150 feet per minute. An unheated pressure roll immediately following the ultrasonic horn was applied to the webs. The pressure roll operated against fixed stops which provided a minimum clearance with the bosses on the anvil roll of about 3 mils. In addition, the pressure roll was loaded with a force $F_2$ sufficient to keep the laminate web from lifting the pressure roll of the fixed stops.

The resultant laminate web exhibited a bonding pattern generally similar to that shown in FIG. 3. The slip layer was temporarily separated from the bonded web assemblage, a pressure sensitive adhesive was applied to the lowermost surface of the moisture barrier layer, and the slip layer was reapplied. The resultant sanitary napkins cut from the web exhibited a physical appearance and configuration generally similar to that shown in FIG. 6. The bonds thus produced securely fastened the various layers, excluding the slip layer, to one another without significantly damaging any of the webs in question. The resultant sanitary napkin exhibited soft, non-abrasive and non-irritating cut edges.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of this invention.

What is claimed is:

1. A resiliently compressible bandage structure suitable for absorbing bodily discharges, said structure being bonded on-the-fly by the input of mechanical energy thereto, said structure comprising:
   (a) a first body contacting layer comprised of a fluid-pervious polymeric material which is softenable by the input of mechanical energy thereto;
   (b) a subjacent moisture absorbent layer comprised of a resiliently compressible material which exhibits a significant interstitial void volume; and
   (c) a moisture barrier layer comprised of a fluid-impervious polymeric material which is softenable by the input of mechanical energy thereto, said moisture barrier layer underlying said moisture absorbent layer and being fused to said body contacting layer adjacent the perimeter of said bandage through the interstitial void volume in said resiliently compressible moisture absorbent layer, said moisture barrier layer being continuously fused to said body contacting layer to form a substantially continuous moisture-impervious seal adjacent the entire perimeter of said bandage to prevent leakage of absorbed bodily discharges contained within said resiliently compressible moisture absorbent layer from reaching the edges of said bandage.

2. The resiliently compressible bandage structure of claim 1, including securement means on the outermost surface of said moisture barrier layer for securing said bandage to the user's apparel when said bandage is placed in service.

3. The resiliently compressible bandage structure of claim 2, wherien said securement means comprises a pressure sensitive adhesive.

4. The resiliently compressible bandage structure of claim 3, wherein said pressure sensitive adhesive is protected prior to use by a layer of silicone treated release paper which is temporarily secured to said bandage structure by said pressure sensitive adhesive.

5. A resiliently compressible bandage structure suitble for absorbing bodily discharges, said structure being bonded on-the-fly by the input of mechanical energy thereto, said structure comprising:
   (a) a first body contacting layer comprised of a fluid-pervious polymeric material which is softenable by the input of mechanical energy thereto;
   (b) a subjacent moisture absorbent layer comprised of a ply of tissue paper and an underlying ply of resiliently compressible material which exhibits a significant interstitial void volume;
   (c) a moisture barrier layer comprised of a fluid-impervious polymeric material which is softenable by the input of mechanical energy thereto underlying said moisture absorbent layer; said body contacting layer being secured directly to said ply of tissue paper by mechanical entanglement, said moisture barrier layer also being secured to said ply of tissue paper by mechanical entanglement after passing through the interstices comprising said void volume in said ply of resiliently compressible material.

6. The resiliently compressible bandage structure of claim 5, wherein said ply of resiliently compressible material is softenable by the same input of mechanical energy required to soften said body contacting and moisture barrier layers, whereby said moisture barrier layer, said ply of tissue paper and said ply of resiliently compressible material are also secured to one another by fusion of said resiliently compressible material.

7. The resiliently compressible bandage structure of claim 5, wherein said ply of resiliently compressible material includes a binder which is softenable by the same input of mechanical energy required to soften said body contacting and moisture barrier layers, whereby said moisture barrier layer, said ply of tissue paper and said ply of resiliently compressible material are also secured to one another by fusion of said binder on said resiliently compressible material.

* * * * *

UNITED STATES PATENT AND TRADEMARK OFFICE
CERTIFICATE OF CORRECTION

PATENT NO. : 4,823,783

DATED : April 25, 1989

INVENTOR(S) : William Willhite, Jr; Gerald M. Weber; Godfrey Reiter

It is certified that error appears in the above-identified patent and that said Letters Patent is hereby corrected as shown below:

First column, third inventor, "Retier" should read -- Reiter -- .

References Cited Section, "3,447,433" should read -- 3,477,433 -- .

Column 2, line 40, "adsorbent" should read -- absorbent -- .

Column 3, line 5, "protruberances" should read -- protuberances -- .

Column 3, line 10, "protruberances" should read -- protuberances -- .

Column 3, line 12, after "wear", first occurrence, insert " -- " .

Column 6, line 17, "therafter" should read -- thereafter -- .

Column 7, line 62, "velocityh" should read -- velocity -- .

Column 10, line 21, "of", first occurrence, should read -- or -- .

Column 11, line 65, "apprent" should read -- apparent -- .

Column 12, line 33, "ato" should read -- at -- .

Column 14, line 46, "applicationof" should read -- application of -- .

Column 14, line 62, "Zellerback" should read -- Zellerbach -- .

Column 15, line 32, "of" should read -- off -- .

Column 16, line 42, after "said moisture absorbent layer;" move "said body ... resiliently compressible material." to the left hand margin of Column 16.

Signed and Sealed this
Twenty-first Day of November, 1989

Attest:

JEFFREY M. SAMUELS

Attesting Officer     Acting Commissioner of Patents and Trademarks

UNITED STATES PATENT AND TRADEMARK OFFICE
CERTIFICATE OF CORRECTION

PATENT NO. : 4,823,783

DATED : April 25, 1989

INVENTOR(S) : William Willhite, Jr., Gerald M. Weber and Godfrey Reiter

It is certified that error appears in the above-identified patent and that said Letters Patent is hereby corrected as shown below:

On the Title page, under RELATED U.S. APPLICATION DATA delete ", abandoned".

Signed and Sealed this

Fifteenth Day of December, 1992

*Attest:*

DOUGLAS B. COMER

*Attesting Officer*      *Acting Commissioner of Patents and Trademarks*